(12) United States Patent
Weber

(10) Patent No.: US 9,364,255 B2
(45) Date of Patent: Jun. 14, 2016

(54) MEDICAL CUTTING DEVICES AND METHODS OF USE

(71) Applicant: BOSTON SCIENTIFIC SCIMED, INC., Maple Grove, MN (US)

(72) Inventor: Jan Weber, Maastricht (NL)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 646 days.

(21) Appl. No.: 13/668,389

(22) Filed: Nov. 5, 2012

(65) Prior Publication Data

US 2013/0116715 A1     May 9, 2013

Related U.S. Application Data

(60) Provisional application No. 61/557,504, filed on Nov. 9, 2011.

(51) Int. Cl.

| | | |
|---|---|---|
| *A61B 17/32* | (2006.01) | |
| *A61B 17/3207* | (2006.01) | |
| *A61F 2/01* | (2006.01) | |
| A61B 17/3205 | (2006.01) | |
| A61B 17/22 | (2006.01) | |

(52) U.S. Cl.
CPC ......... *A61B 17/320725* (2013.01); *A61F 2/013* (2013.01); *A61B 2017/22097* (2013.01); *A61F 2230/0006* (2013.01)

(58) Field of Classification Search
CPC .......... A61B 17/320725; A61B 17/3207; A61B 17/32075; A61B 17/320783; A61B 17/320758; A61B 17/320016; A61B 2017/320791; A61B 2017/22097; A61B 2017/320716; A61B 2017/320733; A61B 2017/320741; A61B 2017/320004; A61B 17/320708; A61B 17/32; A61B 17/32002; A61B 17/320036; A61B 2017/320766; A61B 2017/320775; A61B 2017/320024; A61B 2017/320028; A61B 2017/320032; A61B 2017/32004; A61F 2/013; A61M 2025/109; A61M 25/104; A61M 2005/5006
USPC .......................... 606/159, 170; 604/22, 164.06
See application file for complete search history.

(56) References Cited

U.S. PATENT DOCUMENTS

| | | |
|---|---|---|
| 3,540,431 A | 11/1970 | Mobin-Uddin |
| 3,837,345 A | 9/1974 | Matar |
| 3,952,747 A | 4/1976 | Kimmell, Jr. |
| 4,273,128 A | 6/1981 | Lary et al. |
| 4,425,908 A | 1/1984 | Simon |
| 4,494,531 A | 1/1985 | Gianturco |

(Continued)

FOREIGN PATENT DOCUMENTS

WO     0160262 A1     8/2001

OTHER PUBLICATIONS

U.S. Appl. No. 13/571,552, filed Aug. 10, 2012.

*Primary Examiner* — Melanie Tyson
*Assistant Examiner* — Katherine Schwiker
(74) *Attorney, Agent, or Firm* — Seager, Tufte & Wickhem LLP

(57) ABSTRACT

A cutting device for repairing a heart valve may include a delivery catheter, a cutting unit including an elongate shaft and a plurality of cutting wires, and a plurality of centralizing wires configured to center the cutting unit within a treatment site. A method of repairing a heart valve may include withdrawing a cutting unit through a treatment site while maintaining a plurality centralizing wires in an expanded centering configuration.

18 Claims, 7 Drawing Sheets

(56) References Cited

U.S. PATENT DOCUMENTS

| | | | |
|---|---|---|---|
| 4,619,246 | A | 10/1986 | Molgaard-Nielsen et al. |
| 4,643,184 | A | 2/1987 | Mobin-Uddin |
| 4,650,466 | A | 3/1987 | Luther |
| 4,696,667 | A | 9/1987 | Masch |
| 4,723,549 | A * | 2/1988 | Wholey et al. ............... 606/194 |
| 4,728,319 | A | 3/1988 | Masch |
| 4,765,332 | A | 8/1988 | Fischell et al. |
| 4,817,600 | A | 4/1989 | Herms et al. |
| 4,832,055 | A | 5/1989 | Palestrant |
| 4,840,176 | A | 6/1989 | Ohno |
| 4,990,156 | A | 2/1991 | Lefebvre |
| 4,998,539 | A | 3/1991 | Delsanti |
| 5,009,659 | A | 4/1991 | Hamlin et al. |
| 5,030,201 | A | 7/1991 | Palestrant |
| 5,035,706 | A | 7/1991 | Gianturco et al. |
| 5,047,040 | A | 9/1991 | Simpson et al. |
| 5,069,679 | A | 12/1991 | Taheri |
| 5,078,722 | A | 1/1992 | Stevens |
| 5,152,773 | A | 10/1992 | Redha |
| 5,196,024 | A | 3/1993 | Barath et al. |
| 5,217,484 | A | 6/1993 | Marks |
| 5,226,909 | A | 7/1993 | Evans et al. |
| 5,250,059 | A | 10/1993 | Andreas et al. |
| 5,282,813 | A | 2/1994 | Redha et al. |
| 5,287,858 | A | 2/1994 | Hammerslag et al. |
| 5,320,634 | A | 6/1994 | Vigil et al. |
| 5,324,304 | A | 6/1994 | Rasmussen |
| 5,329,942 | A | 7/1994 | Gunther et al. |
| 5,354,279 | A | 10/1994 | Hoefling et al. |
| 5,370,657 | A | 12/1994 | Irie |
| 5,372,601 | A | 12/1994 | Lary |
| 5,375,612 | A | 12/1994 | Cottenceau et al. |
| 5,383,887 | A | 1/1995 | Nadal |
| 5,417,703 | A | 5/1995 | Brown et al. |
| 5,441,510 | A | 8/1995 | Simpson et al. |
| 5,507,760 | A | 4/1996 | Wynne et al. |
| 5,507,761 | A | 4/1996 | Duer |
| 5,522,825 | A | 6/1996 | Kropf et al. |
| 5,569,277 | A | 10/1996 | Evans et al. |
| 5,601,595 | A | 2/1997 | Smith |
| 5,616,149 | A | 4/1997 | Barath et al. |
| 5,628,761 | A | 5/1997 | Rizik |
| 5,634,942 | A | 6/1997 | Chevillon et al. |
| 5,643,296 | A | 7/1997 | Hundertmark et al. |
| 5,649,953 | A | 7/1997 | Lefebvre et al. |
| 5,709,704 | A | 1/1998 | Nott et al. |
| 5,713,913 | A | 2/1998 | Lary et al. |
| 5,725,543 | A | 3/1998 | Redha et al. |
| 5,797,935 | A | 8/1998 | Barath et al. |
| 5,810,874 | A | 9/1998 | Lefebvre |
| 5,836,968 | A | 11/1998 | Simon et al. |
| 5,836,969 | A | 11/1998 | Kim et al. |
| 5,843,103 | A | 12/1998 | Wulfman |
| 5,853,420 | A | 12/1998 | Chevillon et al. |
| 5,895,402 | A | 4/1999 | Hundertmark et al. |
| 5,902,313 | A | 5/1999 | Redha |
| 5,947,985 | A * | 9/1999 | Imran ............................ 606/159 |
| 5,968,071 | A | 10/1999 | Chevillon et al. |
| 5,976,172 | A | 11/1999 | Homsma et al. |
| 6,009,877 | A | 1/2000 | Edwards et al. |
| 6,013,093 | A | 1/2000 | Nott et al. |
| 6,102,938 | A | 8/2000 | Evans et al. |
| 6,165,187 | A | 12/2000 | Reger |
| 6,238,412 | B1 * | 5/2001 | Dubrul et al. ................. 606/200 |
| 6,241,746 | B1 | 6/2001 | Bosma et al. |
| 6,258,108 | B1 | 7/2001 | Lary |
| 6,267,776 | B1 | 7/2001 | O'Connell |
| 6,331,166 | B1 | 12/2001 | Burbank et al. |
| 6,423,032 | B2 | 7/2002 | Parodi |
| 6,451,036 | B1 | 9/2002 | Heitzmann et al. |
| 6,508,773 | B2 | 1/2003 | Burbank et al. |
| 6,547,803 | B2 | 4/2003 | Seward et al. |
| 6,632,231 | B2 | 10/2003 | Radisch, Jr. |
| 6,709,444 | B1 | 3/2004 | Makower |
| 6,808,531 | B2 | 10/2004 | Lafontaine et al. |
| 7,201,761 | B2 | 4/2007 | Woolfson et al. |
| 7,396,358 | B2 | 7/2008 | Appling |
| 7,517,352 | B2 | 4/2009 | Evans et al. |
| 8,080,026 | B2 | 12/2011 | Konstantino et al. |
| 2004/0204738 | A1 * | 10/2004 | Weber et al. ................... 606/200 |
| 2006/0178685 | A1 | 8/2006 | Melsheimer |
| 2008/0306499 | A1 * | 12/2008 | Katoh et al. ................... 606/159 |
| 2009/0099581 | A1 * | 4/2009 | Kim et al. ...................... 606/159 |
| 2010/0241148 | A1 | 9/2010 | Schon et al. |
| 2010/0324472 | A1 * | 12/2010 | Wulfman ........................ 604/22 |

* cited by examiner

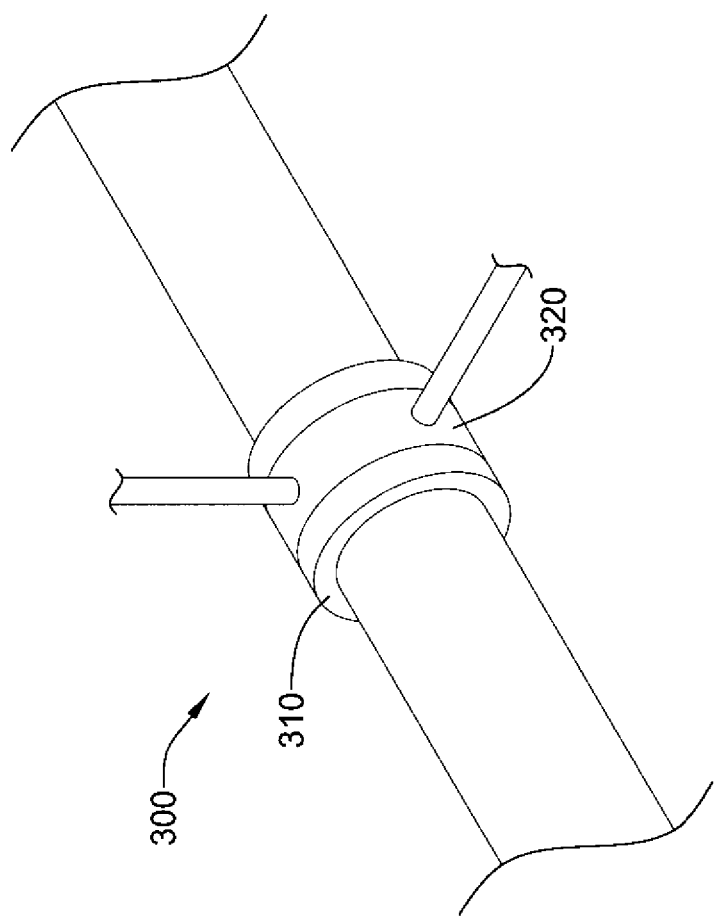

MEDICAL CUTTING DEVICES AND METHODS OF USE

CROSS-REFERENCE TO RELATED APPLICATIONS

None.

TECHNICAL FIELD

The invention relates generally to medical devices and more particularly to medical devices that are adapted for use in repairing heart valves.

BACKGROUND

Aortic valve stenosis is a frequent expression of valvular heart disease, and may often be a leading indicator for valve replacement therapy in Europe and the United States. The prevalence of aortic stenosis tends to increase in older population groups. In some cases, traditional valve replacement surgery is not suitable for patients with higher surgical risk factors. Alternate therapies, and/or linking therapies that may transition an at-risk patient to a more suitable condition for surgery, may be beneficial in improving the lifestyle of patients suffering from aortic valve stenosis.

A continuing need exists for alternative and/or predecessor treatments to traditional valve replacement surgery.

SUMMARY

A percutaneously-deployable cutting device may include a delivery catheter having a lumen extending therethrough, an elongate shaft disposed within the lumen of the delivery catheter, a cutting unit disposed about a distal end of the elongate shaft, the cutting unit including a first mounting ring, a second mounting ring, and a plurality of cutting wires extending from the first mounting ring to the second mounting ring, wherein each of the plurality of cutting wires includes a cutting blade disposed on at least a portion thereof, and a plurality of longitudinally-oriented centralizing wires disposed proximal of the plurality of cutting wires, the plurality of centralizing wires configured to center the cutting unit within a treatment site.

A method of repairing a heart valve may include obtaining a cutting device including a delivery catheter, a cutting unit having a plurality of cutting wires, and a plurality of centralizing wires, advancing the cutting device percutaneously to a treatment site, extending the cutting unit distally from the delivery catheter through the treatment site in a collapsed delivery configuration, actuating the plurality of cutting wires into an expanded cutting configuration, actuating the plurality of centralizing wires into an expanded centering configuration, and withdrawing the cutting unit through the treatment site in the expanded cutting configuration while maintaining the plurality of centralizing wires in the expanded centering configuration.

Although discussed with specific reference to use within the coronary vasculature of a patient, for example to repair a heart valve, medical cutting devices and methods of use in accordance with the disclosure can be adapted and configured for use in other parts of the anatomy, such as the digestive system, the respiratory system, or other parts of the anatomy of a patient.

BRIEF DESCRIPTION OF THE FIGURES

FIG. 7 is a perspective view of a rotatable mounting ring.

Figure 1:
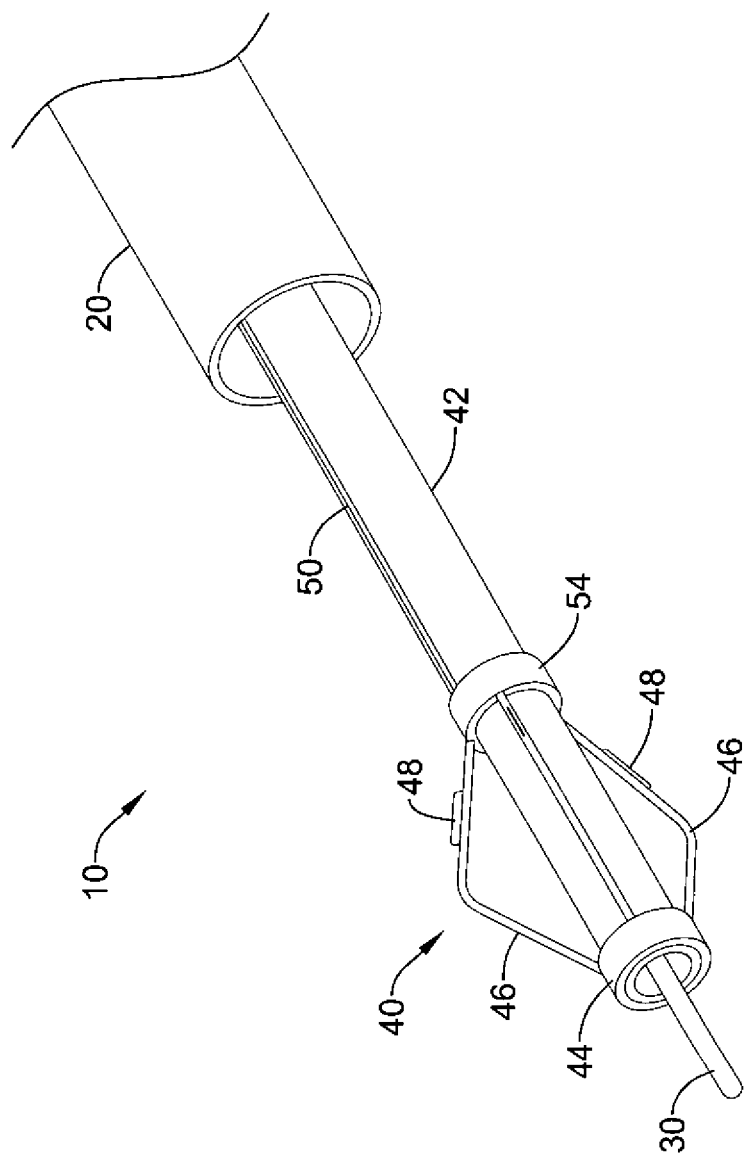
FIG. 1 is a perspective view of an example cutting device.

While the invention is amenable to various modifications and alternative forms, specifics thereof have been shown by way of example in the drawings and will be described in greater detail below. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

The terms "upstream" and "downstream" refer to a position or location relative to the direction of blood flow through a particular element or location, such as a vessel (i.e., the aorta), a heart valve (i.e., the aortic valve), and the like.

All numeric values are herein assumed to be modified by the term "about," whether or not explicitly indicated. The term "about" generally refers to a range of numbers that one of skill in the art would consider equivalent to the recited value (i.e., having the same function or result). In many instances, the term "about" may include numbers that are rounded to the nearest significant figure.

Weight percent, percent by weight, wt %, wt-%, % by weight, and the like are synonyms that refer to the concentration of a substance as the weight of that substance divided by the weight of the composition and multiplied by 100.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following description should be read with reference to the drawings wherein like reference numerals indicate like elements throughout several views. The detailed description and drawings are intended to illustrate but not limit the claimed invention.

A human heart includes several different heart valves, including aortic, pulmonary, mitral, and tricuspid valves, which control the flow of blood to and from the heart. Over time, a heart valve may become obstructed, narrowed, and/or less flexible (i.e., stenosed) due to hardening, calcium deposition, or other factors, thereby reducing the flow of blood through the valve and/or increasing the pressure within the chambers of the heart as the heart attempts to pump the blood through the vasculature. In some cases, aortic valve stenosis may result in the leaflets becoming fused together by calcium deposits, such as, for example, on the aortic or downstream side of the valve. One traditional treatment method is valve replacement, where the stenosed valve is removed and a replacement tissue or mechanical valve is implanted via open heart surgery. For some patients, an alternative to valve replacement may be valve repair, where the native heart valve is repaired percutaneously, to improve the function and/or extend the useful life of the heart valve without subjecting the patient to the invasiveness of open heart surgery.

A typical aortic valve may comprise three leaflets, although two leaflet and four leaflet valves are known to occur in a portion of the population. For simplicity, the following discussion will be described in the context of a three leaflet aortic valve. However, it is fully contemplated that the devices and methods described herein may be adapted for use in the treatment of a two or four (or more) leaflet heart valve and/or a non-aortic heart valve. One of ordinary skill in the art will understand that in the event of treating a non-aortic heart valve, the relative orientations and directions associated with the described devices and methods may be modified to accommodate the specifics (i.e., orientation, location, size, etc.) of the heart valve undergoing treatment.

In some embodiments, a percutaneously-deployable cutting device may be employed to repair a heart valve. A cutting device may be introduced into the vasculature and advanced through the aorta in a retrograde direction across the aortic valve and into the left ventricle in a collapsed, non-cutting or delivery configuration, with or without the aid of a separate delivery catheter. The cutting unit is then deployed to an expanded cutting configuration, and the deployed cutting unit may be used to cut through the stenosis, separating the leaflets and in some cases, removing at least a portion of the stenosis from the leaflets. Once separated, the leaflets may regain a portion or all of their normal function, thereby improving blood flow through the heart valve.

FIG. 1 illustrates an example cutting device 10, which may comprise a delivery catheter 20, a guidewire 30, and a cutting unit 40. The guidewire 30 may be disposed within a lumen of the cutting unit 40 and/or the delivery catheter 20 to serve as a guide for navigating the cutting device 10 through the vasculature to a treatment site (i.e., the heart). The cutting unit 40 may include an elongate shaft 42 having a proximal end and a distal end, a first mounting ring 44, a second mounting ring 54, a plurality of cutting wires 46 configured to actuate between a collapsed delivery configuration and an expanded cutting configuration, and in some embodiments, an actuation wire 50 extending proximally from the cutting unit 40.

In some embodiments, the plurality of cutting wires 46 may comprise two cutting wires 46, three cutting wires 46, four cutting wires 46, or more than four cutting wires 46. The plurality of cutting wires 46 may each have a proximal end, a proximal section adjacent the proximal end, a distal section adjacent the proximal section, and a distal end adjacent the distal section. Each of the plurality of cutting wires 46 may include a cutting blade 48 disposed or mounted on all or a portion of the proximal section such that in the expanded cutting configuration, a cutting edge of the cutting blade 48 is oriented to face in a generally proximal direction. In some embodiments, the proximal section may extend, in the expanded cutting configuration, radially closer to a longitudinal axis of the elongate shaft 42 than the cutting blade 48 towards the proximal end, and the proximal section may extend radially farther from the longitudinal axis than the cutting blade 48 towards the distal end. Consequently, in the expanded cutting configuration, the cutting blades 48 are substantially prevented from contact with a wall of the heart and/or aorta adjacent to the valve being treated.

The first mounting ring 44 may be disposed about the distal end of the elongate shaft 42. In some embodiments, the first mounting ring 44 may be axially fixed in position about the elongate shaft 42. Each of the plurality of cutting wires 46 may have a distal end fixedly attached to the first mounting ring 44 and a proximal end fixedly attached to the second mounting ring 54. In some embodiments, the plurality of cutting wires 46 may be releasably attached to the first mounting ring 44 and/or the second mounting ring 54. The second mounting ring 54 may be disposed about the elongate shaft 42 proximal of the first mounting ring 44. In some embodiments, the second mounting ring 54 may be axially slidable about the elongate shaft 42 and/or rotatable about the elongate shaft 42. The second mounting ring 54 may be actuatable between a first axial position along the elongate shaft 42 and a second axial position along the elongate shaft 42. Accordingly, the relative spacing between the first mounting ring 44 and the second mounting ring 54 may vary with movement of the second mounting ring 54 along the elongate shaft 42. When the second mounting ring 54 is disposed at the first axial position, the cutting unit 40 is configured to be in a collapsed delivery configuration, wherein each of the plurality of cutting wires 46 is disposed in a generally elongated arrangement such that each of the plurality of cutting wires 46 lies generally parallel to the longitudinal axis of the elongate shaft 42. When the second mounting ring 54 is actuated to the second axial position, (i.e., by manipulation of an actuation wire 50, self-biased expansion of the cutting wires 46, other means, or some combination thereof), the second mounting ring 54 is moved axially closer to the first mounting ring 44 along the elongate shaft 42 to achieve an expanded cutting configuration, wherein each of the plurality of cutting wires 46 is formed into a generally arcuate, curved parabolic shape between the first mounting ring 44 and the second mounting ring 54. The apex of the parabolic shape may form a contact point with the wall of the heart, wherein the cutting blade 48 is maintained in a spaced-apart relationship with the wall of the heart to prevent unintended damage or injury to the wall of the heart when the cutting unit 40 is in the expanded cutting configuration.

In operation, the delivery catheter 20 may be advanced along the guidewire 30 to a position adjacent to the treatment site (i.e., the aortic valve). The cutting unit 40, in the collapsed delivery configuration, may be extended from the delivery catheter 20 through the treatment site (i.e., the aortic valve) and into the left ventricle. Once the cutting unit 40 is disposed within the heart, an actuation wire 50 may be manipulated to actuate the second mounting ring 54 distally along the elongate shaft 42, thereby actuating the cutting unit 40 into the expanded cutting configuration. Other means of actuation, as discussed herein, are also contemplated. After the cutting unit 40 has been actuated into the expanded cutting configuration, the cutting unit 40 is slowly withdrawn proximally to bring a portion of the plurality of cutting wires 46 proximal and radially inward of the cutting blades 48 into contact with the valve leaflets. In some embodiments, this non-cutting portion of the plurality of cutting wires 46 may cooperate with the valve leaflets to align the plurality of cutting wires 46, and the cutting blades 48 disposed thereon, with the openings between the valve leaflets. Next (i.e. once aligned), the cutting unit 40 may be slowly withdrawn through the treatment site (i.e., the aortic valve), where the movement of the valve leaflets as the heart continues to beat causes the leaflets to engage with the cutting blades 48 and cut through the stenosis to reestablish proper arrangement and function of the valve leaflets. While withdrawing the cutting unit 40 proximally, the delivery catheter 20 may be held stationary, such that the cutting unit 40 moves proximally relative to the delivery catheter 20 while the delivery catheter 20 is held in a fixed position within the vasculature, or relative to the treatment site. The leaflets' own motion may provide at least a portion of the energy needed to cut through the stenosis. Following the procedure, the cutting unit 40 may be collapsed and re-sheathed within the delivery sheath 20 for withdrawal from the treatment site.

In some instances, the stenosis may be sufficiently rigid, heavy, or otherwise severe enough to move or offset the cutting unit 40 sideways or transversely with respect to the flow of blood through the center of the treatment site (i.e., the aortic valve) as the cutting unit 40 is withdrawn through the treatment site (i.e., the aortic valve). In order to facilitate a centered cutting path, the cutting device 10 may include a plurality of centralizing wires 60. When the cutting unit 40 is properly positioned for deployment, the plurality of cutting wires 46 will open distal or upstream of the treatment site (i.e., the aortic valve) and the plurality of centralizing wires 60 will open proximal or downstream of the treatment site (i.e., the aortic valve), for example, within the vessel lumen (i.e., the aorta and/or the aortic arch). The plurality of centralizing wires 60 may maintain the cutting unit 40 in a substantially centered relationship within the treatment site (i.e., the aortic valve) and/or aligned with a central axis of the vessel lumen (i.e. the aorta and/or the aortic arch).

Figure 3:
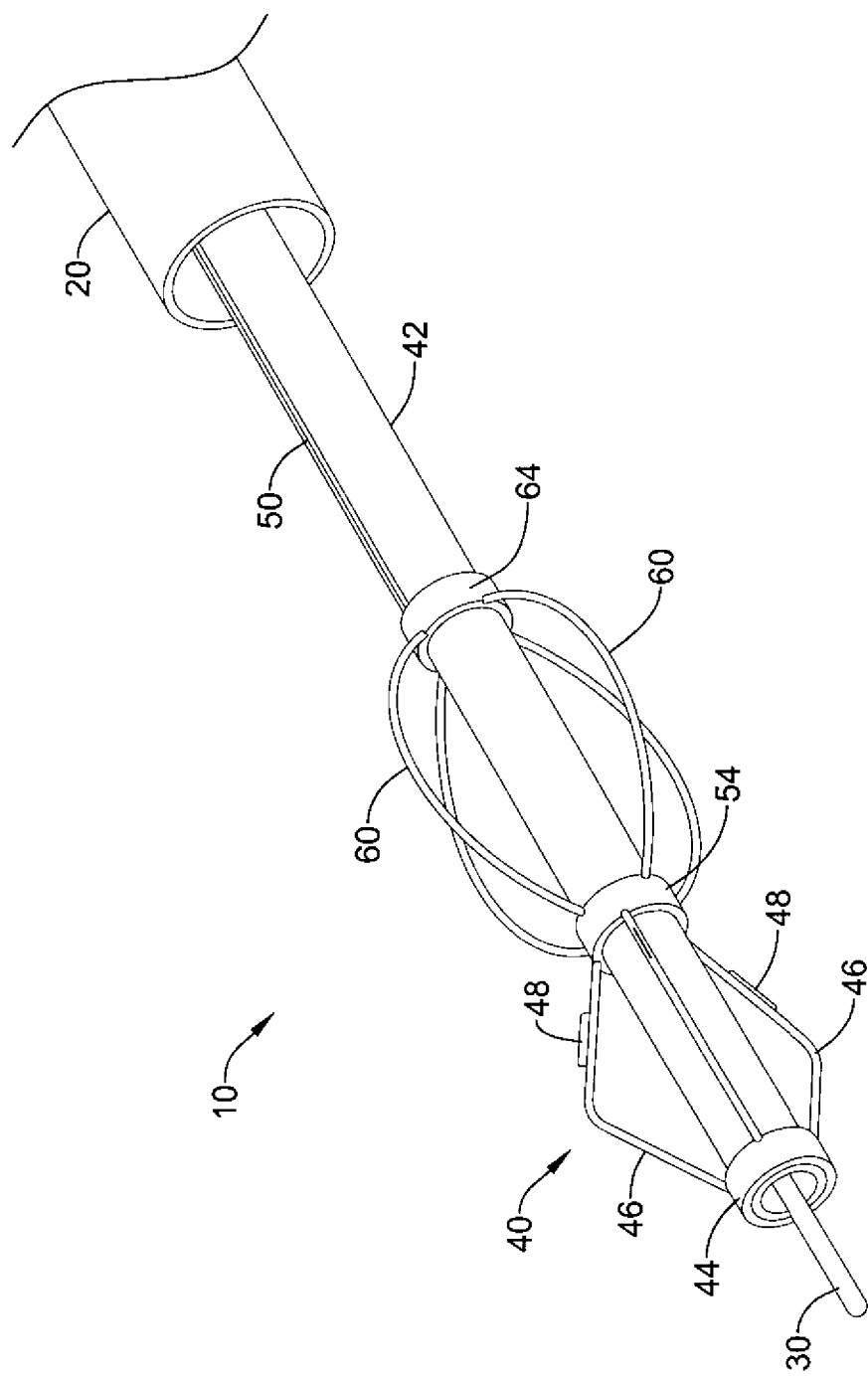
FIG. 3 is a perspective view of the cutting device of FIG. 1 including centralizing wires.

FIG. 3 illustrates the example cutting device 10 of FIG. 1, further including a plurality of centralizing wires 60. In some embodiments, the plurality of centralizing wires 60 may comprise two centralizing wires 60, three centralizing wires 60, four centralizing wires 60, or more than four centralizing wires 60. In some embodiments, the plurality of centralizing wires 60 may be fixedly attached to the cutting unit 40. In some embodiments, the plurality of centralizing wires 60 may be integrally formed with the cutting unit 40. In some embodiments, the plurality of centralizing wires 60 may be releasably attached to the cutting unit 40.

The plurality of centralizing wires 60 may be attached to and/or disposed between the second mounting ring 54 and a third mounting ring 64. The third mounting ring 64 may be axially slidable about the elongate shaft 42 and/or rotatable about the elongate shaft 42. The third mounting ring 64 may move or operate in a manner similar to the second mounting ring 54. The third mounting ring 64 may actuate between a first axial position along the elongate shaft 42 and a second axial position along the elongate shaft 42 that is distal of the first axial position. When the third mounting ring 64 is disposed in the first axial position, the plurality of centralizing wires 60 is configured to be in a collapsed delivery configuration, wherein each of the plurality of centralizing wires 60 is disposed in a generally elongated arrangement such that each of the plurality of centralizing wires 60 lies generally parallel to the longitudinal axis of the elongate shaft 42. When the third mounting ring 64 is advanced to the second axial position, the third mounting ring 64 is moved axially closer to the second mounting ring 54 along the elongate shaft 42 to achieve an expanded centering configuration, wherein each of the plurality of centralizing wires 60 is formed into a generally arcuate, curved parabolic shape between the second mounting ring 54 and the third mounting ring 64.

In some embodiments, each of the plurality of centralizing wires 60 may be longer in length than the plurality of cutting wires 46. When the plurality of cutting wires 46 is actuated to the expanded cutting configuration and the plurality of centralizing wires 60 is actuated to the expanded centering configuration, the longer length of the plurality of centralizing wires 60 may provide a less parabolic shape for the plurality of centralizing wires 60 than the plurality of cutting wires 46, wherein the plurality of centralizing wires 60 form a flatter arc along the apex than the plurality of cutting wires 46. In some embodiments, the generally flatter apex of the plurality of centralizing wires 60 may form a larger contact area with an inner wall of the vessel lumen (i.e., the aorta and/or the aortic arch) than the apex of the plurality of cutting wires 46 may form with the wall of the heart.

Deployment of the plurality of cutting wires 46 and the plurality of centralizing wires 60 illustrated in FIG. 3 may be done by several different means including, but not limited to, self-biased expansion, automatic actuation, manual actuation, or combinations thereof. For example, in some embodiments, cutting wires 46 and/or centralizing wires 60 comprising a shape memory material (i.e., nickel-titanium alloy, shape memory polymer, etc.) may be configured to automatically expand into the deployed or expanded cutting and/or centering configuration, respectively. In some embodiments, one or more actuation wires 50 may be provided, and a user may manually actuate the plurality of cutting wires 46 into the expanded cutting configuration and the plurality of centralizing wires 60 into the expanded centering configuration. For example, in some embodiments, a single actuation wire 50 may actuate both the second mounting ring 54 and the third mounting ring 64 from the first axial position into the second axial position to achieve the expanded cutting configuration and the expanded centering configuration. The actuation wire 50 may extend proximally from the second mounting ring 54 and/or the third mounting ring 64 to a location outside of the vasculature, where the actuation wire 50 may be manually manipulated. After completion of the treatment, the actuation wire 50 may be manually manipulated to return the plurality of cutting wires 46 and the plurality of centralizing wires 60 to the collapsed delivery configuration for removal from the treatment site and/or vasculature. In some embodiments, the second mounting ring 54 and the third mounting ring 64 may each have separate, individually actuatable actuation wires, or no dedicated actuation wires may be present. In some embodiments, other actuation means are contemplated—including, but not limited to, automatic actuation, spring-assisted actuation, computer-assisted or computer-guided actuation, etc.

In operation, the delivery catheter 20 of FIG. 3 may be advanced through the vasculature along the guidewire 30 to a position adjacent to the treatment site (i.e., the aortic valve). The cutting unit 40, in the collapsed delivery configuration, may be extended from the delivery catheter 20 through the treatment site (i.e., the aortic valve) and into the left ventricle such that the plurality of cutting wires 46 is disposed distal or upstream of the treatment site (i.e., the aortic valve) and the plurality of centralizing wires 60 is disposed proximal or downstream of the treatment site (i.e., the aortic valve), with the second mounting ring 54 disposed generally within an opening of the treatment site (i.e., the aortic valve). Once the cutting unit 40 is positioned, the plurality of cutting wires 46 and the plurality of centralizing wires 60 may be actuated (for example, by an actuation wire 50) into the expanded cutting and centering configurations, respectively. After the plurality of cutting wires 46 have been actuated into the expanded cutting configuration, and the plurality of centralizing wires 60 have been actuated into the expanded centering configuration, the cutting unit 40 is slowly withdrawn proximally to bring a portion of the plurality of cutting wires 46 proximal and radially inward of the cutting blades 48 into contact with the valve leaflets. In some embodiments, this non-cutting portion of the plurality of cutting wires 46 may cooperate with the valve leaflets to align the plurality of cutting wires 46, and the cutting blades 48 disposed thereon, with the openings between the valve leaflets. Next (i.e., once aligned), the cutting unit 40 may be slowly withdrawn through the treatment site (i.e., the aortic valve), where the movement of the valve leaflets as the heart continues to beat causes the leaflets to engage with the cutting blades 48 and cut through the stenosis to reestablish proper arrangement and function of the valve leaflets. The leaflets' own motion may provide at least a portion of the energy needed to cut through the stenosis. The plurality of centralizing wires 60 cooperate with the vessel wall (i.e., the aorta and/or aortic arch) to maintain the cutting unit 40 a centered position relative to the treatment site (i.e., the aortic valve). The plurality of centralizing wires 60 and/or the elongate shaft 42 may be sufficiently rigid or stiff as to prevent deflection of the plurality of cutting wires 46 passing through the treatment site (i.e., the stenosed aortic valve), thereby ensuring that the cutting blades 48 are maintained in a centered position relative to the valve as well. Following the procedure, the cutting unit 40, including the plurality of centralizing wires 60, may be collapsed into the delivery configuration and re-sheathed within the delivery sheath 20 for withdrawal from the treatment site.

Figure 4:
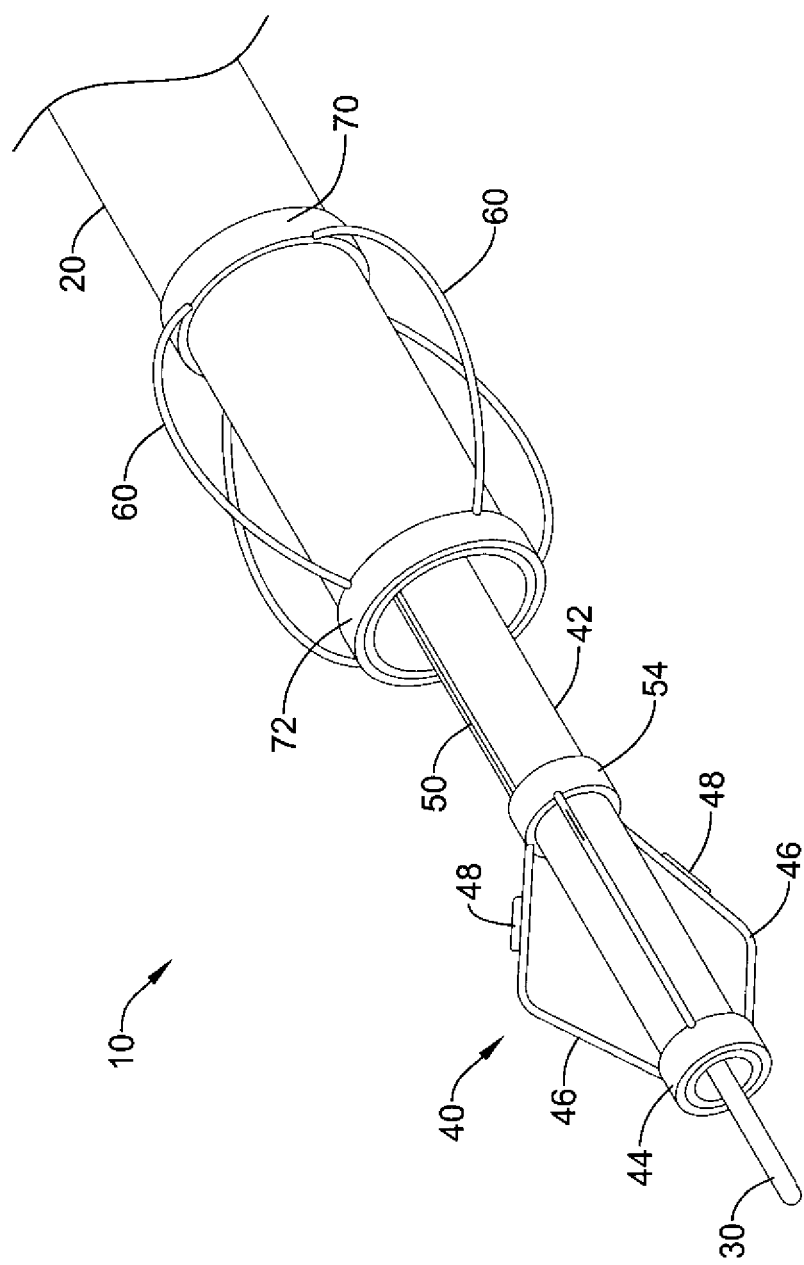
FIG. 4 is a perspective view of the cutting device of FIG. 1 including centralizing wires.

FIG. 4 illustrates the example cutting device 10 of FIG. 1, further including a plurality of centralizing wires 60. In some embodiments, the plurality of centralizing wires 60 may comprise two centralizing wires 60, three centralizing wires 60, four centralizing wires 60, or more than four centralizing wires 60. In some embodiments, the plurality of centralizing wires 60 may be disposed about the distal end of the delivery catheter 20. In some embodiments, the plurality of centralizing wires 60 may be attached to or disposed between a proximal mounting ring 70 and a distal mounting ring 72, disposed about the distal end of the delivery catheter 20. The proximal mounting ring 70 and the distal mounting ring 72 may function relative to the delivery catheter 20 in a manner similar to the second mounting ring 54 and the first mounting ring 44 relative to the elongate shaft 42, respectively. The distal mounting ring 72 may be axially fixed in position about the delivery catheter 20 and the plurality of centralizing wires 60 may be fixedly attached to the proximal mounting ring 70 and/or the distal mounting ring 72. The proximal mounting ring 70 may be axially slidable about the delivery catheter 20 and/or rotatable about the delivery catheter 20. In some embodiments, the plurality of centralizing wires 60 may be releasably attached to the proximal mounting ring 70 and/or the distal mounting ring 72.

The proximal mounting ring 70 may actuate between a first axial position along the delivery sheath 20 and a second axial position along the delivery sheath 20 that is distal of the first axial position. When the proximal mounting ring 70 is disposed in the first axial position, the plurality of centralizing wires 60 is configured to be in a collapsed delivery configuration, wherein each of the plurality of centralizing wires 60 is disposed in a generally elongated arrangement such that each of the plurality of centralizing wires 60 lies generally parallel to a longitudinal axis of the delivery catheter 20. When the proximal mounting ring 70 is advanced to the second axial position, the proximal mounting ring 70 is moved axially closer to the distal mounting ring 72 along the delivery sheath 20 to achieve an expanded centering configuration, wherein each of the plurality of centralizing wires 60 is formed into a generally arcuate, curved parabolic shape between the proximal mounting ring 70 and the distal mounting ring 72.

Similar to other examples described herein, actuation of the plurality of centralizing wires 60 of FIG. 4 may be effected by several different means. For example, the plurality of centralizing wires 60 may be formed from a shape memory material that self-actuates to the expanded centering configuration in the vessel lumen (i.e., the aorta and/or the aortic arch) adjacent the treatment site (i.e., the aortic valve). The plurality of centralizing wires 60 may be actuated by an actuation wire (not shown) fixedly attached to the proximal mounting ring 70 and extending proximally therefrom. Alternatively, the plurality of centralizing wires 60 may be actuated to the expanded centering configuration by a second delivery catheter (not shown) disposed about and axially slidable over the delivery catheter 20, wherein a distal end of the second delivery catheter is configured to abut a proximal face of the proximal mounting ring 70 oriented toward a proximal end of the cutting device 10. The proximal face may be configured to engage a distal end of the second delivery catheter to facilitate distal movement and/or actuation of the proximal mounting ring 70 from the first axial position to the second axial position. In some embodiments, the proximal face may be configured to abut the distal end of the second delivery catheter. In some embodiments, the second delivery catheter may include a distal face at the distal end, wherein the distal face is oriented opposite the proximal face of the proximal mounting ring 70. Distal advancement of the second delivery catheter relative to the delivery catheter 20 may bring the distal end into abutment with the proximal mounting ring 70, wherein further advancement moves the proximal mounting ring 70 distally about the delivery catheter 20 to achieve the expanded centering configuration. In some embodiments, other actuation means are contemplated—including, but not limited to, automatic actuation, spring-assisted actuation, computer-assisted or computer-guided actuation, etc.

In operation, the delivery catheter 20 of FIG. 4 may be advanced through the vasculature along the guidewire 30 to a position adjacent to the treatment site (i.e., the aortic valve). The cutting unit 40, in the collapsed delivery configuration, may be extended from the delivery catheter 20 through the treatment site (i.e., the aortic valve) and into the left ventricle such that the plurality of cutting wires 46 is disposed distal or upstream of the treatment site (i.e., the aortic valve). The delivery catheter 20 and the plurality of centralizing wires 60 are disposed proximal or downstream of the treatment site (i.e., the aortic valve), for example, within the vessel lumen (i.e. the aorta and/or the aortic arch). Once the cutting unit 40 is positioned, the plurality of cutting wires 46 may be actuated into the expanded cutting configuration and the plurality of centralizing wires 60 may be actuated into the expanded centering configuration. After the cutting unit 40 has been actuated into the expanded cutting configuration, the cutting unit 40 is slowly withdrawn proximally to bring a portion of the plurality of cutting wires 46 proximal and radially inward of the cutting blades 48 into contact with the valve leaflets. In some embodiments, this non-cutting portion of the plurality of cutting wires 46 may cooperate with the valve leaflets to align the plurality of cutting wires 46, and the cutting blades 48 disposed thereon, with the openings between the valve leaflets. Next (i.e., once aligned), the cutting unit 40 may be slowly withdrawn through the treatment site (i.e., the aortic valve), where the movement of the valve leaflets as the heart continues to beat causes the leaflets to engage with the cutting blades 48 and cut through the stenosis to reestablish proper arrangement and function of the valve leaflets. The leaflets' own motion may provide at least a portion of the energy needed to cut through the stenosis. While withdrawing the cutting unit 40 proximally, the delivery catheter 20 may be held stationary, such that the cutting unit 40 moves proximally relative to the delivery catheter 20 while the delivery catheter 20 is held in a fixed position within the vasculature (or relative to the treatment site). The plurality of centralizing wires 60 cooperates with the vessel wall (i.e., the aorta and/or the aortic arch) to maintain the delivery catheter 20 in a centered position within the vessel lumen (i.e., the aorta and/or the aortic arch). The cutting unit 40 is simultaneously maintained in a centered position within the treatment site (i.e., the aortic valve). The plurality of centralizing wires 60 and/or the elongate shaft 42 may be sufficiently rigid or stiff as to prevent deflection of the cutting unit 40 (or a portion thereof) passing through the treatment site (i.e., the stenosed aortic valve), thereby ensuring that the cutting blades 48 are maintained in a centered position relative to the treatment site (i.e., the aortic valve) as well. Following the procedure, the cutting unit 40 may be collapsed and re-sheathed within the delivery sheath 20, and the plurality of centralizing wires 60 may be collapsed into the delivery configuration along the delivery sheath 20, for withdrawal from the treatment site and/or vasculature.

Figure 5:
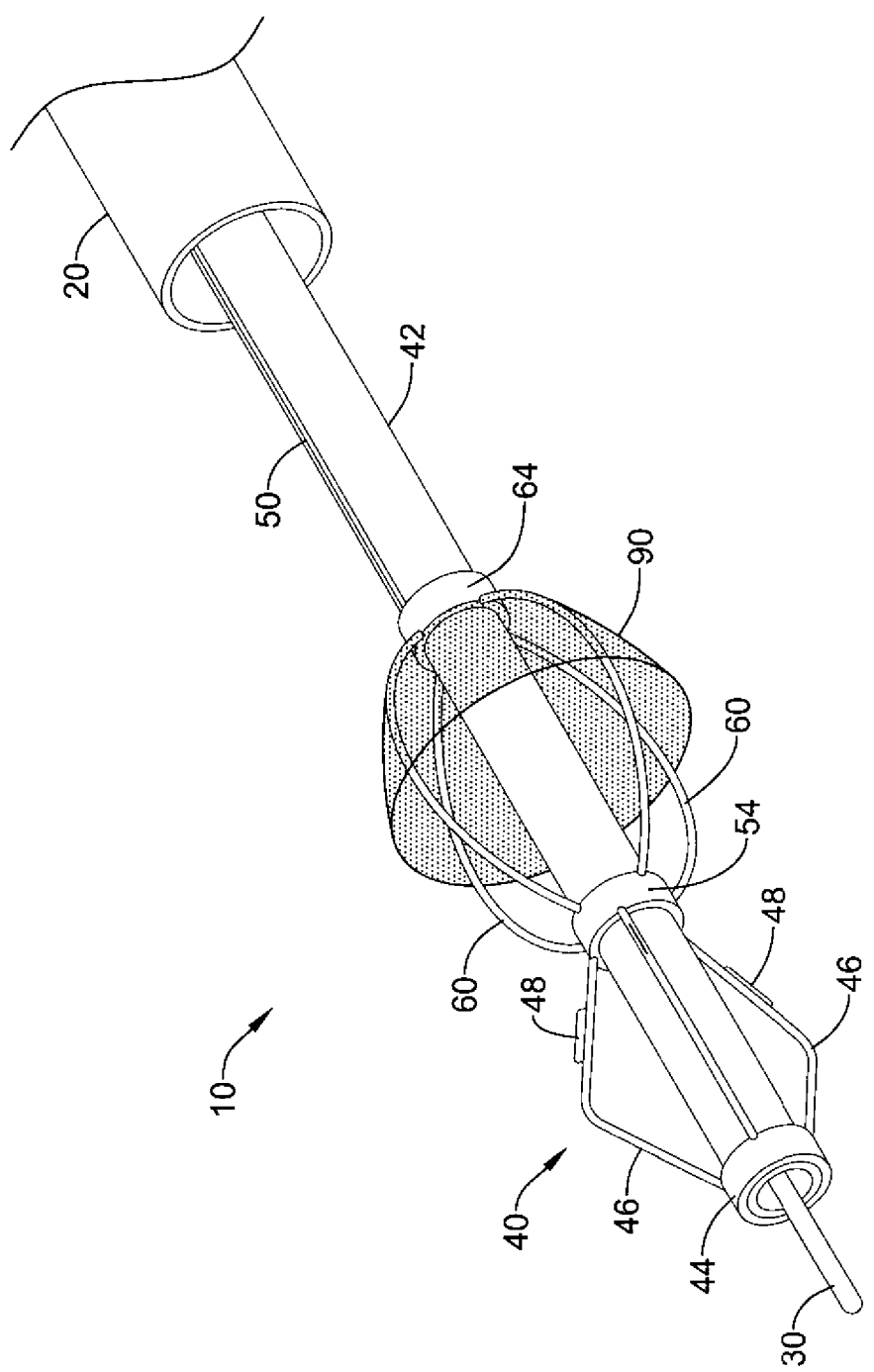
FIG. 5 is a perspective view of the cutting device of FIG. 3 including a filter.

FIG. 5 illustrates the example cutting device 10 of FIG. 3, further including a distal protection filter 90. The distal protection filter 90 may be mounted to or within (not shown) a proximal portion of the plurality of centralizing wires 60. The distal protection filter 90 may have a mouth or major opening facing distally toward the plurality of cutting wires 46 and a closed end or apex attached to the third mounting ring 64. The distal protection filter 90 may be configured to substantially span the entire inner diameter of the vessel lumen (i.e. the aorta and/or the aortic arch) when the plurality of centralizing wires 60 is disposed in the expanded centering configuration. The distal protection filter 90 may be formed as a mesh, braid, or membrane having a plurality of apertures therethrough to facilitate perfusion blood flow through the distal protection filter 90 while capturing material larger than the apertures. The distal protection filter 90 may be formed from metallic, polymeric, or composite materials, or other combinations thereof as desired. The distal protection filter 90 may include one or more coatings disposed thereon, such as an anti-thrombus coating, a hydrophilic coating, a hydrophobic coating, or other coatings suitable for the procedure being performed. In some embodiments, the distal protection filter 90 may include a tether or closure element (not shown) configured to close the mouth and retain captured material within the filter 90 prior to withdrawal from the treatment site and/or vasculature.

Figure 6:
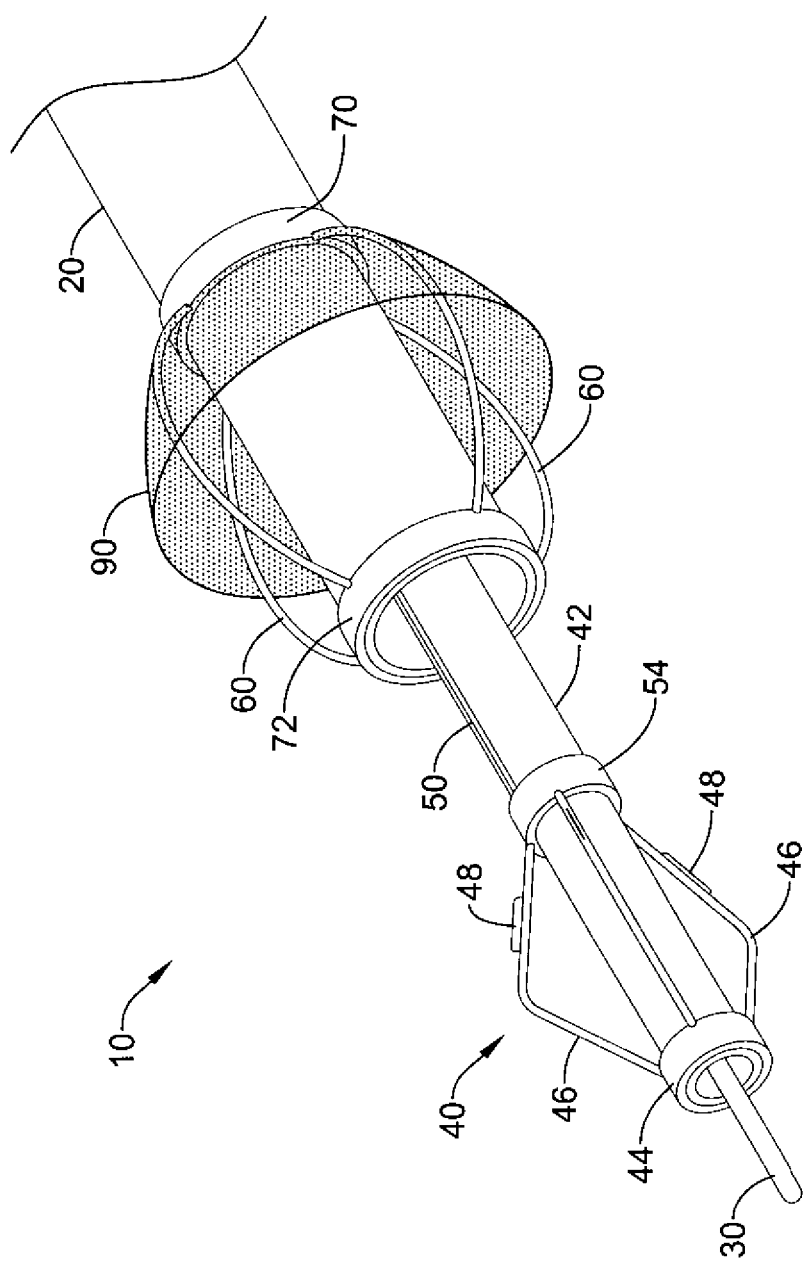
FIG. 6 is a perspective view of the cutting device of FIG. 4 including a filter.

FIG. 6 illustrates the example cutting device 10 of FIG. 4, further including a distal protection filter 90. The distal protection filter 90 may be mounted to or within (not shown) a proximal portion of the plurality of centralizing wires 60. The distal protection filter 90 may have a mouth or major opening facing distally toward the cutting unit 40 and a closed end or apex attached to the proximal mounting ring 70. The distal protection filter 90 may be configured to substantially span the entire inner diameter of the vessel lumen (i.e., the aorta and/or the aortic arch) when the plurality of centralizing wires 60 is disposed in the expanded centering configuration. The distal protection filter 90 may be formed as a mesh, braid, or membrane having a plurality of apertures therethrough to facilitate perfusion blood flow through the distal protection filter 90 while capturing material larger than the apertures. The distal protection filter 90 may be formed from metallic, polymeric, or composite materials, or other combinations thereof as desired. The distal protection filter 90 may include one or more coatings disposed thereon, such as an anti-thrombus coating, a hydrophilic coating, a hydrophobic coating, or other coatings suitable for the procedure being performed. In some embodiments, the distal protection filter 90 may include a tether or closure element (not shown) configured to close the mouth and retain captured material within the filter 90 prior to withdrawal from the treatment site and/or vasculature.

FIG. 7 illustrates an example mounting ring 300. In some embodiments of the cutting device 10 described herein, none, one, a plurality or more than one, or all of the mounting rings (i.e., ref. 44, 54, 64, 70, 72) may take the form of mounting ring 300. In other words, there may be zero, one, or more mounting rings 300 present in the cutting device 10 described above. The mounting ring 300 may comprise a mounting portion 310 and a rotating portion 320. The plurality of cutting wires 46 and/or the plurality of centralizing wires 60 may be fixedly attached to the rotating portion 320. In some embodiments, the plurality of cutting wires 46 and/or the plurality of centralizing wires 60 may be releasably attached to the rotating portion 320. The rotating portion 320 may include an annular ring rotatably disposed about the mounting portion 310. In some embodiments, an outer diameter of the mounting portion 310 and an outer diameter of the rotating portion 320 may be substantially equal so as to form a smooth outer surface along the entire length of the mounting ring 300. The mounting portion 310 may include a recessed portion which receives the rotating portion 320 therein, or a portion having a reduced outer diameter which receives the rotating portion 320 thereon. The rotating portion 320 may facilitate alignment of the plurality of cutting wires 46 with the openings between the valve leaflets of an aortic valve undergoing a treatment procedure. The rotating portion 320 may limit abrasion, shear forces, or general trauma to the vessel wall (i.e., the aorta and/or the aortic arch) that may occur if the plurality of centralizing wires 60 is subjected to movement of the delivery catheter 20 by permitting the delivery catheter 20 to rotate relative to the plurality of centralizing wires 60.

The mounting portion 310 may be disposed about the elongate shaft 42 and/or the delivery catheter 20. In some embodiments, the mounting portion 310 may be fixedly attached to the underlying elongate shaft 42 and/or delivery catheter 20. In some embodiments, the mounting portion 310 may be slidably and/or rotatably attached to the underlying elongate shaft 42 and/or delivery catheter 20. In other words, the mounting portion 310 may be slidable and/or rotatable relative to the elongate shaft 42 and/or the delivery catheter 20.

Although not expressly illustrated, a distal portion of the delivery catheter 20 and/or the elongate shaft 42 may be configured to include a predetermined bending configuration aligning with the curve of the aorta and/or the aortic arch. The elongate shaft 42 may include a directional bending component (not shown) that aligns the elongate shaft 42 with the delivery catheter 20 through the curve of the aorta and/or the aortic arch. For example, the elongate shaft 42 may include a metallic wire or strip (not shown) embedded within a wall, or disposed within a lumen within the wall, of the elongate shaft 42. The metallic wire or strip may be flattened or otherwise configured to have a predetermined or preferential bending direction. As the elongate shaft 42 is advanced through the delivery catheter 20, the elongate shaft 42 and the delivery catheter 20 will align such that the cutting unit, and the plurality of cutting wires 46, will assume a predetermined orientation within the treatment site (i.e., the aortic valve) corresponding to the openings between the valve leaflets.

The plurality of cutting wires 46 and/or the plurality of centralizing wires 60 may be made from materials such as metals, metal alloys, polymers, metal-polymer composites, or other suitable materials, and the like. Some examples of some suitable materials may include stainless steels (e.g. 304v stainless steel or 316L stainless steel), nickel-titanium alloys (e.g., nitinol, such as super elastic or linear elastic nitinol), nickel-chromium alloys, nickel-chromium-iron alloys, cobalt alloys, nickel, titanium, platinum, or alternatively, a polymer material, such as a high performance polymer, or other suitable materials, and the like. The word nitinol was coined by a group of researchers at the United States Naval Ordinance Laboratory (NOL) who were the first to observe the shape memory behavior of this material. The word nitinol is an acronym including the chemical symbol for nickel (Ni), the chemical symbol for titanium (Ti), and an acronym identifying the Naval Ordinance Laboratory (NOL).

Each cutting wire 46 can be formed from spring wire. For example, in some embodiments, the spring wire can be spring steel or stainless steel. In some embodiments, the spring wire can be a shape memory alloy such as nitinol. As illustrated, each cutting wire 46 is generally circular in cross-section. Each cutting wire 46 may have other geometries. A cutting wire 46 may be flattened, with an oval cross-section. A cutting wire 46 may be square, rectangular, triangular, or other multi-sided geometries, in cross-section. A cutting wire 46 with a non-circular cross-section may have advantages in performance or manufacturing. Alternatively, a cutting wire 46 with a circular cross-section may have performance advantages.

In some embodiments, cutting wires 46 formed from spring wire may be used to bias the cutting unit 40 into the collapsed delivery configuration. In other embodiments, other biasing mechanisms such as springs may be used. In the collapsed delivery configuration, the cutting blades 48 are effectively retracted, and cannot cut tissue. If the plurality of cutting wires 46 is axially compressed by moving the appropriate mounting ring(s), the plurality of cutting wires 46 may bend and deflect outward. When the compressive force is removed, the plurality of cutting wires 46 may straighten out and once again bias the cutting unit 40 into the collapsed delivery configuration. In some embodiments, the plurality of centralizing wires 60 may operate in the same manner and exhibit the same or similar characteristics as the plurality of cutting wires 46.

As noted, each of the plurality of cutting wires 46 may be formed from a metallic alloy such as nitinol or other suitable material. The first mounting ring 44, the second mounting ring 54, and/or the third mounting ring 64 may be formed from the same or similar metallic materials, or other suitable materials, such as a polymeric or composite material. The plurality of cutting wires 46 and the plurality of centralizing wires 60 may be attached to the first mounting ring 44, the second mounting ring 54, and/or the third mounting ring 64 using appropriate attachment techniques. Some examples of attachment techniques include soldering, brazing, adhesion attachment, mechanical interlocking or attachment, and thermal bonding such as sonic or laser welding or RF.

Similarly, each of the plurality of centralizing wires 60 may be formed from a metallic alloy such as nitinol or other suitable material. In some embodiments, the plurality of centralizing wires 60 may be made from a widened strip of polymeric material, such as nylon, polyester, polyamide, polyurethane, and the like. In some embodiments, the plurality of centralizing wires 60 may be wider than the plurality of cutting wires 46 to distribute the centralizing forces across a greater area of the vessel wall (i.e., the aorta and/or the aortic arch).

The proximal mounting ring 70 and/or the distal mounting ring 72 may be formed from the same or similar metallic materials, polymeric materials, composite materials, or other suitable materials. The plurality of centralizing wires 60 may be attached to the proximal mounting ring 70 and/or the distal mounting ring 72 using appropriate attachment techniques. Some examples of attachment techniques include soldering, brazing, adhesion attachment, mechanical interlocking or attachment, and thermal bonding such as sonic or laser welding or RF. It is contemplated that the mounting portion 310 and the rotating portion 320 of the mounting ring 300 may be made from a single material, two different materials, or two similar materials, and the like, as appropriate.

The plurality of cutting wires 46 may each include a cutting blade 48 that is attached to the cutting wire 46. If the blade 48 is not integral with the cutting wire 46, the blade 48 is attached or connected to the cutting wire 46 using any of a broad variety of suitable attachment techniques, depending upon the types of materials being joined. For example, the blade can be attached to the wire using joining techniques such as adhesive bonding, welding, soldering, brazing, crimping, friction fitting, thermal bonding, and the like.

The cutting blade 48 may be made of any suitable material that would provide the desired cutting characteristics. In some embodiments, the cutting blade 48 may be made from metallic materials or alloys, ceramic materials, composite materials, and the like. In some embodiments, the cutting blade 48 can be a diamond blade that enables nearly force-free cutting. In some embodiments, the diamond blade can have a cutting edge that is only several atoms wide and a radius of about 3 nanometers. As illustrated, each of the plurality of cutting wires 46 has a single cutting blade 48 secured to a proximal portion of the cutting wire 46. While not expressly illustrated, each of the plurality of cutting wires 46 may include a plurality of cutting blades 48 disposed along the cutting wire 46.

Portions of the cutting device 10 may be made of, may be doped with, may include a layer of, or otherwise may include a radiopaque material. Radiopaque materials are understood to be materials capable of producing a relatively bright image on a fluoroscopy screen or another imaging technique such as X-ray during a medical procedure. This relatively bright image aids the user of device in determining its location. For example, one or more of the mounting rings described above (i.e., ref. 44, 54, 70, etc.) may include or be formed from a radiopaque material. Suitable materials can include, but are not limited to, bismuth subcarbonate, iodine, gold, platinum, palladium, tantalum, tungsten or tungsten alloy, and the like.

Figure 2:
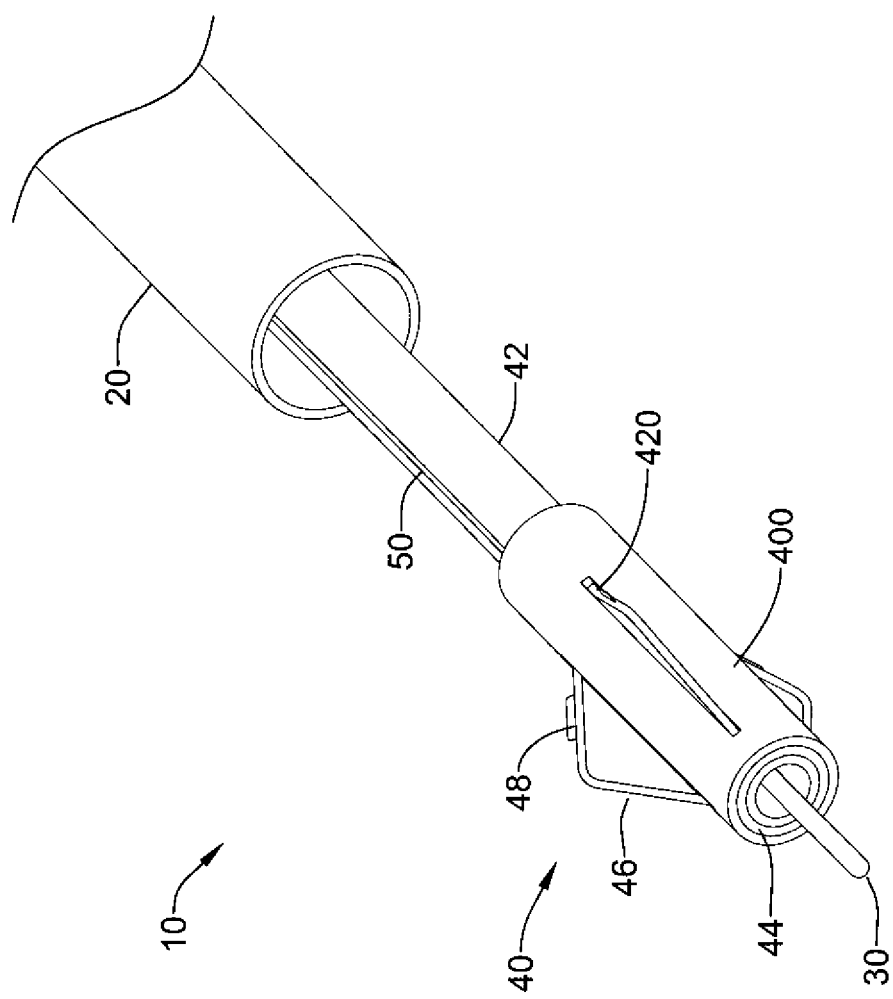
FIG. 2 is a perspective view of the cutting device of FIG. 1 including a protective housing.

FIG. 2 illustrates the example cutting device 10 of FIG. 1 in the expanded cutting configuration, further including a protective housing 400. A suitable housing 400 is illustrated in FIG. 2 as a cylindrical tube. The housing 400 may be fixedly attached to the first mounting ring 44. The housing 400 may be configured to permit the second mounting ring 54 to axially actuate within the housing 400. In other words, the second mounting ring 54 may be axially movable relative to the housing 400. Additionally, the housing 400 may be added to the cutting unit 40 as desired. That is to say, a housing 400 may be included in any or all examples and embodiments of the cutting device 10 disclosed herein.

The housing 400 may include one or more longitudinal slots 420 configured to align with each of the plurality of cutting wires 46. For example, if the cutting unit 40 has three equally-spaced cutting wires 46, the housing 400 may have three equally-spaced longitudinal slots 420. In some embodiments, each of the one or more longitudinal slots 420 may be dimensioned to accommodate the particular cutting wire 46 and cutting blade 48 present therein and/or extending therethrough. In some embodiments, the one or more longitudinal slots 420 may be dimensioned smaller than the cutting wires 46, or may be absent altogether, as in some embodiments the plurality of cutting wires 46 and cutting blades 48 may cut through and penetrate the housing 400 if the housing 400 is formed of a sufficiently soft material.

The housing 400 may be made of any suitable material, for example, a polymeric material, a metal, a metal alloy, a metal-polymer composite, or the like. Examples of suitable polymers may include polyurethane, a polyether-ester such as ARNITEL® available from DSM Engineering Plastics, a polyester such as HYTREL® available from DuPont, a linear low density polyethylene such as REXELL®, a polyamide such as DURETHAN® available from Bayer or CRISTAMID® available from Elf Atochem, an elastomeric polyamide, a block polyamide/ether, a polyether block amide such as PEBA available under the trade name PEBAX®, silicones, polyethylene, Marlex high-density polyethylene, polyetheretherketone (PEEK), polyimide (PI), and polyetherimide (PEI), a liquid crystal polymer (LCP) alone or blended with other materials. Examples of suitable metallic materials may include stainless steels (e.g. 304v stainless steel), nickel-titanium alloys (e.g., nitinol. such as super elastic or linear elastic nitinol), nickel-chromium alloys, nickel-chromium-iron alloys, cobalt alloys, nickel, titanium, platinum, or other suitable materials, and the like.

In some embodiments, the housing 400 may have an outer diameter in the range of about 18 to 23 French. In some embodiments, the housing 400 may represent a catheter structure such as a guide catheter and in such embodiments may be substantially longer than the housing 400 illustrated in FIG. 2. For example, if the housing 400 is a guide catheter it may be in the range of about 100 to 150 centimeters in length. In some embodiments, the housing 400 may have an inner diameter configured to accommodate the cutting unit 40 therein, such that the cutting blades 48 are prevented from contact with the treatment site (i.e., the aortic valve) when the cutting unit 40 is disposed in the collapsed delivery configuration, and an outer diameter configured to fit within a particular treatment site. In some embodiments, the housing 400 may have an outer diameter that permits blood flow between an exterior of the housing 400 and the wall of the treatment site (i.e. the heart and/or aorta). In some embodiments, the housing 400 may include one or more ports or openings (not illustrated) that permit blood to pass through the interior of the housing 400 and thereby permit continued blood flow past the treatment site.

It should be understood that although the above discussion was focused on a cutting device and methods of use within the coronary vascular system of a patient, other embodiments of cutting devices or methods in accordance with the invention can be adapted and configured for use in other parts of the anatomy of a patient. For example, devices and methods in accordance with the invention can be adapted for use in the digestive or gastrointestinal tract, such as in the mouth, throat, small and large intestine, colon, rectum, and the like. For another example, devices and methods can be adapted and configured for use within the respiratory tract, such as in the mouth, nose, throat, bronchial passages, nasal passages, lungs, and the like. Similarly, the cutting devices described herein with respect to percutaneous deployment may be used in other types of surgical procedures as appropriate. For example, in some embodiments, the cutting units may be deployed in a non-percutaneous procedure, including an open heart procedure. Devices and methods in accordance with the invention can also be adapted and configured for other uses within the anatomy.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

We claim:

1. A percutaneously-deployable cutting device comprising:
   a delivery catheter having a lumen extending therethrough;
   an elongate shaft disposed within the lumen of the delivery catheter;
   a cutting unit disposed about a distal end of the elongate shaft, the cutting unit including a first mounting ring, a second mounting ring, and a plurality of cutting wires extending from the first mounting ring to the second mounting ring, the cutting unit selectively actuatable between a collapsed delivery configuration and an expanded cutting configuration;
   wherein in the collapsed delivery configuration, each of the plurality of cutting wires is disposed in a generally elongated arrangement along the elongate shaft, and in the expanded cutting configuration, the second mounting ring is disposed axially closer to the first mounting ring along the elongate shaft than in the collapsed delivery configuration and each of the plurality of cutting wires extends radially outward from the elongate shaft in a generally arcuate shape forming an apex between the first mounting ring and second mounting ring where each cutting wire is at its farthest radial distance from the elongate shaft;
   wherein each of the plurality of cutting wires includes a cutting blade disposed on only a proximal side of the apex; and
   a plurality of longitudinally-oriented centralizing wires disposed proximal of the plurality of cutting wires, the plurality of centralizing wires configured to center the cutting unit within a treatment site.

2. The percutaneously-deployable cutting device of claim 1, the cutting unit further including a housing having a plurality of longitudinal slots each corresponding to one of the plurality of cutting wires;
   wherein in the collapsed delivery configuration, the plurality of cutting wires is disposed within the housing, and in the expanded cutting configuration, at least a portion of each of the plurality of cutting wires extends through the plurality of longitudinal slots and outside of the housing.

3. The percutaneously-deployable cutting device of claim 1, further including an actuation wire attached to the cutting unit.

4. The percutaneously-deployable cutting device of claim 3, wherein axial movement of the actuation wire selectively actuates the cutting unit between the collapsed delivery configuration and the expanded cutting configuration.

5. The percutaneously-deployable cutting device of claim 4, wherein the first mounting ring is axially fixed in position along the elongate shaft, and the actuation wire is fixedly attached to the second mounting ring.

6. The percutaneously-deployable cutting device of claim 1, wherein each cutting blade is disposed on its respective cutting wire such that in the expanded cutting configuration, the cutting blade is maintained in a spaced-apart relationship with a plane disposed generally parallel to the elongate shaft and tangent to the apex of its respective cutting wire.

7. The percutaneously-deployable cutting device of claim 1, wherein the plurality of centralizing wires extends from the second mounting ring to a third mounting ring disposed about the elongate shaft.

8. The percutaneously-deployable cutting device of claim 7, wherein the third mounting ring is slidably disposed about the elongate shaft.

9. The percutaneously-deployable cutting device of claim 7, wherein an actuation wire is fixedly attached to the third mounting ring.

10. The percutaneously-deployable cutting device of claim 7, further including a distally-opening filter disposed about the elongate shaft proximal of the plurality of cutting wires.

11. The percutaneously-deployable cutting device of claim 1, wherein the plurality of centralizing wires extends from a proximal mounting ring disposed about the delivery catheter to a distal mounting ring disposed about the delivery catheter.

12. The percutaneously-deployable cutting device of claim 11, wherein the proximal mounting ring is slidably disposed about the delivery catheter and the distal mounting ring is axially fixed in position along the delivery catheter.

13. The percutaneously-deployable cutting device of claim 11, further including a distally-opening filter disposed about the delivery catheter.

14. A method of repairing a heart valve, comprising:
obtaining a cutting device comprising:
a delivery catheter having a lumen extending therethrough;
an elongate shaft disposed within the lumen of the delivery catheter;
a cutting unit disposed about a distal end of the elongate shaft, the cutting unit including a first mounting ring, a second mounting ring, and a plurality of cutting wires extending from the first mounting ring to the second mounting ring;
wherein each of the plurality of cutting wires includes a cutting blade disposed on at least a portion thereof; and
a plurality of longitudinally-oriented centralizing wires disposed on the delivery catheter proximal of the plurality of cutting wires, the plurality of centralizing wires configured to center the cutting unit within a treatment site;
advancing the cutting device percutaneously to a treatment site;
extending the cutting unit distally from the delivery catheter through the treatment site in a collapsed delivery configuration, to a position distal of the treatment site, while leaving the delivery catheter with the plurality of centralizing wires proximal of the treatment site;
actuating the plurality of cutting wires distal of the treatment site into an expanded cutting configuration;
actuating the plurality of centralizing wires proximal of the treatment site into an expanded centering configuration; and
withdrawing the cutting unit proximally through the treatment site in the expanded cutting configuration while maintaining the plurality of centralizing wires in the expanded centering configuration.

15. The method of claim 14, wherein withdrawing the cutting unit through the treatment site includes maintaining the delivery catheter in a fixed position as the cutting unit is withdrawn.

16. The method of claim 14, wherein the treatment site defines a longitudinal axis generally aligned with a flow of blood from upstream to downstream.

17. The method of claim 16, wherein the plurality of centralizing wires maintains the cutting unit generally aligned with the longitudinal axis.

18. The method of claim 14, wherein the cutting unit is selectively actuatable between a collapsed delivery configuration and an expanded cutting configuration, wherein in the collapsed delivery configuration, each of the plurality of cutting wires is disposed in a generally elongated arrangement along the elongate shaft, and in the expanded cutting configuration, the second mounting ring is disposed axially closer to the first mounting ring along the elongate shaft than in the collapsed delivery configuration and each of the plurality of cutting wires extends radially outward from the elongate shaft in a generally arcuate shape forming an apex between the first mounting ring and second mounting ring where each cutting wire is at its farthest radial distance from the elongate shaft, wherein the cutting blade included on at least a portion of each of the plurality of cutting wires is disposed on only a proximal side of the apex.

* * * * *